United States Patent
Nirogi et al.

(10) Patent No.: US 9,802,896 B2
(45) Date of Patent: Oct. 31, 2017

(54) PROCESS FOR LARGE SCALE PRODUCTION OF N-[4-(1-CYCLOBUTYL PIPERIDIN-4-YLOXY) PHENYL]-2-(MORPHOLIN-4-YL) ACETAMIDE DIHYDROCHLORIDE

(71) Applicant: SUVEN LIFE SCIENCES LIMITED, Hyderabad (IN)

(72) Inventors: Ramakrishna Nirogi, Hyderabad (IN); Anil Karbhari Shinde, Hyderabad (IN); Ramasastri Kambhampati, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 15/504,210

(22) PCT Filed: Oct. 20, 2014

(86) PCT No.: PCT/IN2014/000666
§ 371 (c)(1),
(2) Date: Feb. 15, 2017

(87) PCT Pub. No.: WO2016/027275
PCT Pub. Date: Feb. 25, 2016

(65) Prior Publication Data
US 2017/0260135 A1    Sep. 14, 2017

(30) Foreign Application Priority Data
Aug. 16, 2014 (IN) .......................... 4010/CHE/2014

(51) Int. Cl.
*C07D 211/46* (2006.01)

(52) U.S. Cl.
CPC .................................. *C07D 211/46* (2013.01)

(58) Field of Classification Search
CPC ..................................................... C07D 211/46
See application file for complete search history.

(56) References Cited

FOREIGN PATENT DOCUMENTS

WO    2012114348    8/2012

OTHER PUBLICATIONS

International Search Report, European Patent Office, International Application No. PCT/IN2014/000666, dated Feb. 12, 2015.

*Primary Examiner* — Rebecca Anderson
(74) *Attorney, Agent, or Firm* — IpHorgan Ltd.

(57) ABSTRACT

The present, invention relates to a process for large scale production of N-[4-(1-Cyclobutyl piperidin-4-yloxy) phenyl]-2-(morpholin-4-yl) acetamide dihydrochloride of formula (I).

(I)

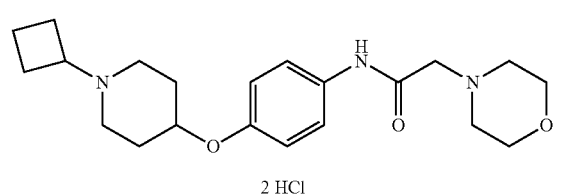

2 HCl

16 Claims, No Drawings

PROCESS FOR LARGE SCALE PRODUCTION OF N-[4-(1-CYCLOBUTYL PIPERIDIN-4-YLOXY) PHENYL]-2-(MORPHOLIN-4-YL) ACETAMIDE DIHYDROCHLORIDE

CROSS REFERENCE TO RELATED APPLICATIONS

This application is a national stage completion application of PCT Application No. PCT/IN2014/000666, filed Oct. 20, 2014, and claims the benefit of Indian Application No. 4010/CHE/2014, filed Aug. 16, 2014.

FIELD OF INVENTION

The present invention relates to a process for large scale production of N-[4-(1-Cyclobutyl piperidin-4-yloxy) phenyl]-2-(morpholin-4-yl) acetamide dihydrochloride of formula (I).

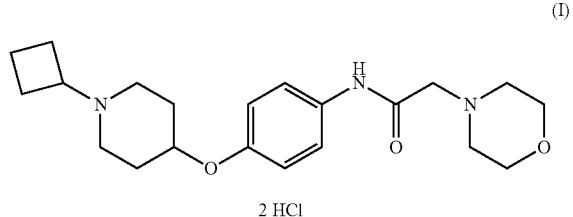 [SMILES: O=C(CN1CCOCC1)Nc1ccc(OC2CCN(C3CCC3)CC2)cc1]

BACKGROUND OF THE INVENTION

N-[4-(1-Cyclobutyl piperidin-4-yloxy) phenyl]-2-(morpholin-4-yl) acetamide dihydrochloride, is a promising pharmaceutical agent, which is potent and selective Histamine $H_3$ receptor ligand intended for the symptomatic treatment of cognitive disorders, dementia, attention deficit hyperactivity disorder, epilepsy, sleep disorders, sleep apnea, obesity, schizophrenia, eating disorders and pain. N-[4-(1-Cyclobutyl piperidin-4-yloxy) phenyl]-2-(morpholin-4-yl) acetamide dihydrochloride and its synthesis is disclosed by Ramakrishna et al. in WO2012114348.

Currently N-[4-(1-Cyclobutyl piperidin-4-yloxy) phenyl]-2-(morpholin-4-yl) acetamide dihydrochloride has completed preclinical studies and is ready to enter human clinical trials. The demand for N-[4-(1-Cyclobutyl piperidin-4-yloxy) phenyl]-2-(morpholin-4-yl) acetamide dihydrochloride as a drug substance has increased substantially with the advent of its clinical testing. The future need for much larger amounts is projected due to the intended commercialization of N-[4-(1-Cyclobutyl piperidin-4-yloxy) phenyl]-2-(morpholin-4-yl) acetamide dihydrochloride.

For the person skilled in art, it is a well known fact that various parameters will change during the manufacture of a compound on a large scale when compared to the synthetic procedures followed in laboratory. Therefore, there is a need to establish and optimize large scale manufacturing process. The process for the preparation of N-[4-(1-Cyclobutyl piperidin-4-yloxy) phenyl]-2-(morpholin-4-yl) acetamide dihydrochloride disclosed in WO2012114348 was proved to be unsatisfactory for adaptation to the large scale manufacturing. Hence it is highly desirable to establish optimized manufacturing process of N-[4-(1-Cyclobutyl piperidin-4-yloxy) phenyl]-2-(morpholin-4-yl) acetamide dihydrochloride of formula (I), which is amenable to the large scale manufacturing of the compound.

SUMMARY OF THE INVENTION

The main object of the present invention is to provide a large scale, well optimized manufacturing process for N-[4-(1-Cyclobutyl piperidin-4-yloxy) phenyl]-2-(morpholin-4-yl) acetamide dihydrochloride of formula (I).

Another object of this invention is to show the compatibility of the process to produce N-[4-(1-Cyclobutyl piperidin-4-yloxy) phenyl]-2-(morpholin-4-yl) acetamide dihydrochloride of formula (I) on a large scale using standard larger scale chemical process equipment.

Yet another object of this invention is to provide a commercial process for the production of N-[4-(1-Cyclobutyl piperidin-4-yloxy) phenyl]-2-(morpholin-4-yl) acetamide dihydrochloride of formula (I) on a larger scale.

DETAILED DESCRIPTION OF THE INVENTION

The large scale manufacturing process for preparation of N-[4-(1-Cyclobutyl piperidin-4-yloxy) phenyl]-2-(morpholin-4-yl) acetamide dihydrochloride of formula (I) of the present invention is illustrated by the Scheme-1 given herein:

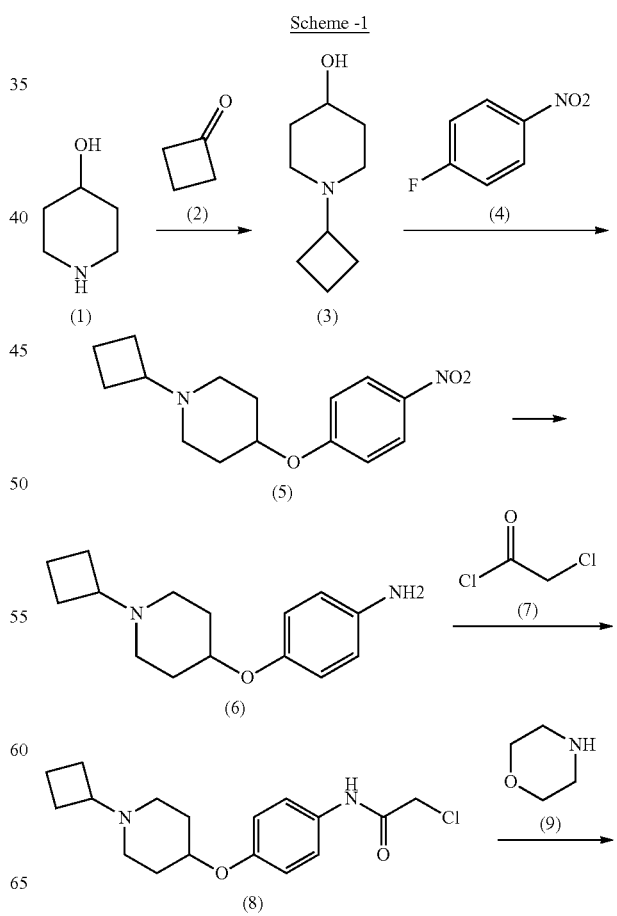

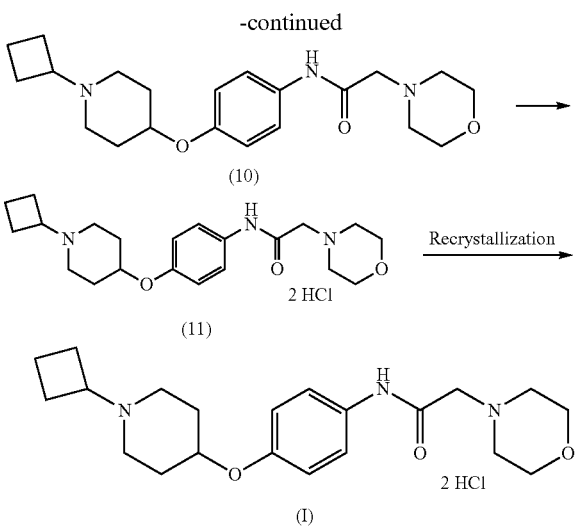

Step (i): coupling of 4-hydroxy piperidine of formula (1) with cyclobutanone of formula (2) in presence of sodium triacetoxy borohydride in a suitable solvent to obtain 1-cyclobutylpiperidin-4-ol of formula (3). The solvent used in the reaction can be selected from halohydrocarbons, preferably ethylene dichloride. This reaction is carried out at a temperature of 20° C. to 30° C., preferably 25° C. to 30° C. The duration of the reaction may range from 12 hours to 14 hours, preferably from a period of 13 hours to 13.5 hours.

Step (ii): coupling of 1-cyclobutylpiperidin-4-ol of formula (3) with 4-fluoro-1-nitrobenzene of formula (4) in a suitable solvent and base to obtain 4-(1-cyclobutylpiperidin-4-yloxy)-1-nitrobenzene of formula (5). The solvent used in the reaction can be selected from ethers, preferably tetrahydrofuran. The base used in the reaction can be selected from alkali metal hydrides, preferably sodium hydride. This reaction is carried out at temperature of 30° C. to 45° C., preferably 35° C. to 40° C. The duration of the reaction may range from 5 hours to 6 hours, preferably from a period of 5.5 hours to 6 hours.

Step (iii): reduction of 4-(1-cyclobutylpiperidin-4-yloxy)-1-nitrobenzene of formula (5) using ammonium chloride and iron powder, in a suitable solvent to obtain 4-(1-cyclobutylpiperidin-4-yloxy) aniline of formula (6). The solvent used in the reaction can be selected from aqueous alcohols, preferably aqueous ethyl alcohol. This reaction is carried out at temperature of 70° C. to 85° C., preferably 75° C. to 80° C. The duration of the reaction may range from 3 hours to 5 hours, preferably for a period of 4 hours.

Step (iv): reaction of 4-(1-cyclobutylpiperidin-4-yloxy) aniline of formula (6) with chloroacetylchloride of formula (7) in a suitable solvent and base to obtain 2-chloro-N-[4-(1-cyclobutyl piperidin-4-yloxy)phenyl]acetamide of formula (8). The solvent used in reaction can be selected from ethers, preferably tetrahydrofuran. The base used in reaction can be selected from alkali metal carbonates, preferably potassium carbonate. This reaction is carried out at a temperature of −10° C. to 0° C., preferably −10° C. to −5° C. The duration of the reaction may range from 4.5 to 5.5 hours, preferably for a period of 5 hours.

Step (v): reaction of 2-chloro-N-[4-(1-cyclobutyl piperidin-4-yloxy)phenyl]acetamide of formula (8) with morpholine of formula (9) in a suitable solvent and base to obtain N-[4-(1-cyclobutyl piperidin-4-yloxy) phenyl]-2-(morpholin-4-yl) acetamide of formula (10). The solvent used in the reaction can be selected from nitrile solvents, preferably acetonitrile. The base used in the reaction can be selected from alkalimetal carbonates, preferably potassium carbonate. This reaction is carried out at temperature of 75° C. to 85° C., preferably 80° C. to 82° C. The duration of the reaction may range from 20 hours to 30 hours, preferably for a period of 24 hours to 26 hours.

Step (vi): converting N-[4-(1-Cyclobutyl piperidin-4-yloxy) phenyl]-2-(morpholin-4-yl) acetamide of formula (10) in presence of isopropanolic hydrochloride and isopropanol to N-[4-(1-cyclobutyl piperidin-4-yloxy) phenyl]-2-(morpholin-4-yl) acetamide dihydrochloride of formula (11). This reaction is carried out at a temperature of 20° C. to 30° C., preferably 25° C. to 30° C. The duration of the reaction may range from 7 hours to 8.5 hours, preferably from a period of 7.5 hours to 8 hours.

Step (vii): recrystallization of N-[4-(1-Cyclobutyl piperidin-4-yloxy) phenyl]-2-(morpholin-4-yl) acetamide dihydrochloride of formula (11) in presence of isopropanol and methanol to obtain N-[4-(1-Cyclobutyl piperidin-4-yloxy) phenyl]-2-(morpholin-4-yl) acetamide dihydrochloride of formula (I). This reaction is carried out at a temperature of 58° C. to 63° C., preferably 62° C. to 63° C. The duration of the reaction may range from 4 hours to 5 hours, preferably for a period of 4.5 hours.

The details of the invention are given in Example provided below.

Example 1: Preparation of N-[4-(1-Cyclobutyl piperidin-4-yloxy) phenyl]-2-(morpholin-4-yl) acetamide dihydrochloride Step (i): Preparation of 1-cyclobutylpiperidin-4-ol Ethylene dichloride (235 L) was charged into the reactor at 20-25° C. followed by 4-hydroxy piperidine (9.5 Kg, 93.92 M). The mass was stirred for ~15 minutes to obtain a clear solution. Then cyclobutanone (7.9 Kg, 112.71 M) was charged into the reactor at 20-25° C. and stirred the mass for 90 minutes at the same temperature. The mass was cooled to 15-20° C. and started lot wise addition of sodium triacetoxy borohydride (39.9 Kg, 188.26 M) maintaining the mass temperature below 25° C. in ~110 minutes. After completion of addition, the mass was stirred for 30 minutes at ~20° C. The mass temperature was raised to 25-30° C. and maintained at the same temperature for ~13.1 hours, while monitoring the progress of the reaction by Thin Layer Chromatography (TLC). After completion of the reaction, water (112 L) was charged into the reactor at 25-30° C. The mass was then cooled to 15-20° C. and pH of the reaction mass was adjusted to 13.0-13.5 with a solution of aqueous sodium hydroxide (24.6 Kg of sodium hydroxide dissolved in 106 L of demineralised water (DM water) maintaining the mass temperature below 20° C. in about 1 hour 20 minutes. In the meanwhile, nutsche filter with hyflow bed (using 4.75 Kg hyflow and 47.5 L DM water) was made ready for filtration of dirt and sodium acetate salt, for the purpose of clean layer separations during extraction of the product. The reaction mass was filtered through nutsche and the nutsche was washed with 23.75 L of ethylene dichloride. The filtrate containing the product was collected into clean and dedicated containers. The combined filtrate and washings were transferred to a reactor, stirred 15 minutes and settled for 15 minutes at 25-30° C. The bottom organic layer (containing the product) was collected in dedicated containers and the mass was dried over anhydrous sodium sulfate (9.5 Kg). The supernatant, clean, dry organic layer was taken in a reactor and solvent was removed by distillation under vacuum maintaining mass temperature below 50° C. The residual crude mass was cooled to 25-30° C.

2nd Extraction of the Aqueous Layer:

The aqueous layer separated as above was taken in a reactor and charged dichloromethane (DCM) (56 L) at 25-30° C. The mass was stirred 15 minutes and settled for 15 minutes. The bottom organic layer (containing product) was separated into dedicated containers. The aqueous layer was collected and taken for 3rd extraction.

3rd Extraction of the Aqueous Layer:

The aqueous layer: separated as above was taken in a reactor and charged DCM (56 L) at 25-30° C. The mass was stirred 15 minutes and settled for 15 minutes. The bottom organic layer (containing product) was separated into dedicated containers. The aqueous layer was collected and taken for 4th extraction.

4th Extraction of the Aqueous Layer:

The aqueous layer separated as above was taken in a reactor and charged DCM (56 L) at 25-30° C. The mass was stirred 15 minutes and settled for 15 minutes. The bottom organic layer (containing product) was separated into dedicated containers. The aqueous layer was collected and taken for 5th extraction.

5th Extraction of the Aqueous Layer:

The aqueous layer separated as above was taken in a reactor and charged dichloromethane (56 L) at 25-30° C. The mass was stirred 15 minutes and settled for 15 minutes. The bottom organic layer (containing product) was separated into dedicated containers. The aqueous layer was collected in dedicated containers and kept aside.

The organic layer obtained from second extraction to fifth extraction was combined and dried over anhydrous sodium sulfate (13.5 Kg). The supernatant, clean, dry organic layer was taken in the reactor, containing the crude product obtained from first extraction, and solvent was removed by distillation under reduced pressure (>500 mm Hg) maintaining mass temperature below 50° C. The residual mass was cooled to 25-30° C. and collected the technical product (14.36 Kg).

Yield: 98.49%;

$^1$H-NMR ($\delta$ ppm, CDCl$_3$): 1.55-1.69 (5H, m), 1.83-2.02 (8H, m), 2.65-2.69 (3H, m), 3.66-3.70 (1H, m);

Mass (m/z): 156.2 (M+H)$^+$.

Step (ii): Preparation of
4-(1-cyclobutylpiperidin-4-yloxy)-1-nitrobenzene

Tetrahydrofuran (THF) (43.2 L) was charged into a Stainless steel reactor (SS reactor) at 25-30° C. under nitrogen atmosphere followed by addition of sodium hydride (5.22 Kg) maintaining mass temperature at 25-30° C. under nitrogen atmosphere. The contents were stirred for 15 minutes at 25-30° C. The temperature of the reaction mass was raised to 35-40° C.

THF (56.7 L) was charged into another SS reactor it 25-30° C. under nitrogen atmosphere by the addition of above obtained step (i) material (13.5 Kg, 86.96 M). The mass was stirred for 15 minutes at 25-30° C. to obtain a clear solution. The resulting solution was added to the above reactor containing sodium hydride in THF, maintaining the mass temperature of the main reactor at 35-40° C. over a period of ~45 minutes under nitrogen atmosphere. The resulting mass was further stirred for 90 minutes at 35-40° C.

In the meanwhile THF (35.8 L) was charged into another SS reactor at 25-30° C. under nitrogen atmosphere, followed by the addition of 4-fluoro-1-nitrobenzene (14.72 Kg, 104.32 M). The contents of the reactor were stirred for 15 minutes at 25-30° C. to obtain a clear solution. The clear solution, thus obtained, was slowly transferred to the main reactor in ~45 minutes maintaining the mass temperature of the main reactor at 35-40° C. The temperature of the reaction mass was further maintained at 35-40° C. for 5 hours under stirring and under nitrogen atmosphere, while monitoring the progress of the reaction by TLC. After completion of the reaction, the reaction mass was cooled to 15-20° C.

Charged water (675 L) into another SS reactor under nitrogen atmosphere. The contents of the reactor were cooled to 5-10° C. Then the reaction mass from the main reactor was transferred carefully to this reactor containing water, maintaining the mass temperature below 20° C. in ~45 minutes. The resulting mass was further stirred for 30 minutes maintaining the temperature at 15-20° C. The solid mass was centrifuged and the mother liquors were collected in dedicated containers. The cake on the centrifuge was washed with water (2×135 L) and spin dried to obtain technical product (19.80 Kg).

Purity: 99.5%.

Purification:

Dissolved the technical product obtained as above (19.80 Kg) in ~200 L of 10% aqueous acetic acid solution (~20.59 Kg acetic acid diluted with 180 L with water) at 25-30° C.

1st Toluene Extraction:

Stirred 15 minutes and then charged toluene (33 L) at 25-30° C. Stirred 15 minutes and settled for 15 minutes and layers separated. The top organic layer containing the impurities was kept aside in a dedicated container.

2nd Toluene Extraction:

The lower aqueous product layer was taken into the reactor again and charged toluene (33 L) at 25-30° C. Stirred 15 minutes and settled for 15 minutes and layers separated. The top organic layer containing the impurities was kept aside in the dedicated container.

3rd Toluene Extraction:

The lower aqueous product layer was taken again into the reactor and charged toluene (25 L) at 25-30° C. Stirred 15 minutes and settled for 15 minutes and layers separated. The top organic layer containing the impurities was kept aside in the dedicated container.

The aqueous product layer was charged into the reactor at 25-30° C. The mass was cooled to 10-15° C. pH of the reaction mass was adjusted to 11.5-12.0 with 20% w/v aqueous sodium hydroxide solution (prepared by dissolving 15.44 Kg sodium hydroxide flakes in 69.3 L of DM water) while maintaining mass temperature at 10-15° C. for 1.45 hours. The resulting mass was stirred for 15 minutes at 25-30° C. at pH 11.55. The solids that separated were centrifuged. The cake was washed with (40 L×2) DM water and the product was spin dried (19.9 Kg), Yield: 53.56%

Purity: 99.52%.

$^1$H-NMR ($\delta$ ppm, CDCl$_3$): 1.58-1.73 (2H, m), 1.84-1.93 (4H, m), 2.02-2.06 (4H, m), 2.19 (2H, s), 2.62 (2H, s), 2.71-2.76 (1H, m), 4.45 (1H, s), 6.93-6.95 (2H, d, J=9.07 Hz), 8.18-8.20 (2H, d, J=9.02 Hz);

Mass (m/z): 277.2 (M+H)$^+$.

The aqueous layer (obtained after centrifuging and washing the product) was collected in dedicated containers for isolation of the second crop.

Step (iii): Preparation of
4-(1-cyclobutylpiperidin-4-yloxy) aniline

The reaction was done in a SS reactor under nitrogen blanket. DM Water (33.59 L) was charged into a SS reactor at 25-30° C. followed by iron powder (10.43 Kg, 186.75 M, 1:4 ratio) under stirring. Then ammonium chloride (11.5 Kg, 215 M) was charged at 25-30° C. and stirred the contents for 15 minutes at 25-30° C. The mass temperature was raised slowly to 95-100° C. and maintained at that temperature (95-100° C.) for ~90 minutes. The mass was cooled to 75-80° C.

In the meanwhile, ethyl alcohol (128.7 L) was charged into another reactor at 25-30° C., followed by addition above obtained compound (19.9 Kg). The contents were stirred for 15 minutes and then raised the mass temperature to 50-55° C., where by a clear solution was obtained. The mass was slowly transferred to the main reactor, containing the activated iron powder at 78-80° C. over a period of ~70 minutes. The mass was further stirred for 3 hours, while maintaining the mass temperature at 75-80° C. The progress of the reaction was monitored by TLC. After completion of the reaction, the reaction mass was cooled to 25-30° C. and filtered through nutsche, containing hyflow bed. The filtrate was collected into dedicated containers. The bed was washed with 3×32.18 L of ethyl alcohol and collected the washings into dedicated containers. The combined filtrate was charged into a clean SS reactor at 25-30° C. All the volatiles are distilled off under reduced pressure (>500 mm Hg) maintaining the mass temperature below 55° C. The residual mass was cooled to 25-30° C. and charged DM water (32.18 L). The pH of the reaction mass was adjusted to 9.0-10.0 with 91 L of sodium carbonate solution (prepared by dissolving 21.5 Kg of sodium carbonate in 80 L of DM water), while maintaining the mass temperature at 25-30° C. Final pH is 9.14. The solid mass, separated in the reactor, was centrifuged and collected the filtrate in dedicated containers. The product was spin dried (20.34 Kg).

Ethylacetate (EtOAc) (80 L) was charged into a clean SS reactor at 25-30° C. followed by the wet cake (20.34 Kg) obtained above. The mass was stirred for 15 minutes at 25-30° C. Then added DM water (32 L) and further stirred the mass for 15 minutes and settled for 15 minutes. The aqueous layer was separated and collected in dedicated containers.

The organic layer containing the product was filtered through nutsche filter through hyflow bed (formed with 5.15 Kg hyflow and 26 L water) and filtrate was collected in dedicated containers. The bed was washed with EtOAc (13 L). The combined organic layer and EtOAc washings were charged into a clean SS reactor. Charged 20 L DM water, stirred for 15 minutes and settled for 15 minutes at 25-30° C. The aqueous layer is separated and the organic layer was dried over anhydrous sodium sulfate (20 Kg).

The clean, dried organic layer was charged into a reactor at 25-30° C. Solvent was distilled off under reduced pressure (>500 mm Hg) below 50° C. (Solvent recovered: 70 L). The residual product was cooled to 25-30° C. and unloaded into dedicated containers (12.30 Kg) and sent for complete analysis.

Weight of the product: 12.3 Kg (wet with solvent EtOAc: 9.1%),

Yield (on dry basis): 97.5%;

Purity: 97.79%;

IR (cm$^{-1}$): 3424, 3345, 2943, 1627, 1509, 1229, 1168, 1044, 821;

$^1$H-NMR (δ ppm, DMSO): 1.49-1.61 (4H, m), 1.71-1.83 (4H, m), 1.92-1.97 (5H, m), 2.52-2.53 (2H, m), 3.99-4.04 (1H, m), 4.59 (2H, bs), 6.46-6.48 (2H, d, J=8.60 Hz), 6.61-6.63 (2H, d, J=8.66 Hz);

Mass (m/z): 247.4 (M+H)$^+$.

Step (iv): Preparation of 2-chloro-N-[4-(1-cyclobutyl piperidin-4-yloxy) phenyl] acetamide The reaction was done in a SS reactor under nitrogen blanket. THF (89.6 L) was charged into a Glass reactor (GLR) at 25-30° C. followed by addition of above obtained material (11.2 Kg on dry basis, 45.46 M). The contents were stirred 15 minutes. Then charged anhydrous potassium carbonate (K$_2$CO$_3$) powder (12.54 Kg, 90.73 M) into the reactor and stirred the mass for 15 minutes at 25-30° C. The reaction mass was cooled to −10 to −5° C. by circulating brine in the jacket. Then a solution of chloroacetylchloride (6.72 Kg, 59.5 M) dissolved in THF (44.8 L) was slowly introduced into the reactor through a holding tank, under nitrogen atmosphere, in ~2.5 hours maintaining the mass temperature at −10 to −5° C. The reaction mass was further maintained under stirring at −10 to −5° C. for another 2 hours while monitoring the progress of the reaction by TLC.

After completion of the reaction, slow addition of chilled DM water (186 L) through the addition funnel started at −10 to −5° C. Towards the end of addition of DM water (addition time 45 minutes), it was so adjusted that the mass temperature reached 10-15° C. After completion of addition of DM water the mass temperature was raised to 25-30° C.

1$^{st}$ Extraction:

Ethyl acetate (112 L) charged into the reactor at 25-30° C. The mass was stirred 30 minutes and settled for 30 minutes. Layers separated and the organic product layer was collected in dedicated containers.

2$^{nd}$ Extraction:

The aqueous layer obtained as above was charged into the reactor followed by EtOAc (112 L) at 25-30° C. The mass was stirred 30 minutes and settled for 30 minutes. Layers separated and the organic product layer and the aqueous layer were collected in dedicated containers.

The combined organic layer, obtained from the above extractions, was charged into a clean GLR followed by the addition of 116 L of brine solution (prepared by dissolving 33.6 Kg sodium chloride in 112 L DM water) at 25-30° C. The mass was stirred for 30 minutes and settled for 30 minutes at 25-30° C. The aqueous layer was separated and collected in dedicated containers. The organic product layer was dried over anhydrous sodium sulfate (22.4 Kg). The volume of the organic layer was 360 L. The organic layer obtained as above was charged into a clean GLR at 25-30° C. Solvent was distilled off under reduced pressure (>500 mm Hg) maintaining mass temperature below 55° C. (volume of recovered solvent; 178 L). The mass was cooled to 25-30° C. Solid mass separated in the reactor.

Recrystallization

Isopropanol (72.8 L) was charged into the reactor containing the solids (~13.5 Kg) at 25-30° C., followed by methanol (~58.2 L) at 25-30° C. Stirred the reaction mass at 25-30° C. for 30 minutes. The mass temperature was raised slowly to reflux temperature and maintained at reflux till a clear solution is obtained (~30 minutes). Then the mass was cooled to 25-30° C. and stirred the mass for 60 minutes. The mass was further cooled to ~12-15° C., stirred for 30 minutes and centrifuged the material. The cake on the centrifuge was washed with 2×7 L isopropanol (25-30° C.) and spin dried thoroughly.

The wet cake (11.2 Kg) was dried in a vacuum tray drier (VTD) for ~4 hours at 40-50° C. to obtain crystallized product (9.7 Kg).

Yield: 66.12%;
Purity (by HPLC): 99.56%;
IR (cm$^{-1}$): 3307, 3278, 2951, 1670.43, 1612, 1554.69, 1508.4, 1240.28, 1171.81, 1047.39, 953.84, 832.32;
$^1$H-NMR (δ ppm, DMSO): 1.53-1.61 (4H, m), 1.72-1.74 (2H, m), 1.87-1.99 (6H, m), 2.49-2.53 (2H, m), 2.64-2.68 (1H, m), 4.19 (2H, s), 4.24-4.29 (1H, m), 6.88-6.90 (2H, d, J=8.96 Hz), 7.44-7.46 (2H, d, J=8.96 Hz), 10.12 (1H, s);
Mass (m/z): 323.3, 325.2 (M+H)$^+$.

Mother liquor obtained, after recrystallization and centrifuging the product, was processed for isolating second crop.

Step (v): Preparation of N-[4-(1-cyclobutyl piperidin-4-yloxy) phenyl]-2-(morpholin-4-yl) acetamide Acetonitrile (141 L) was charged into the GLR at 25-30° C. under nitrogen atmosphere, followed by addition of the above obtained material (9.4 Kg, 29.11 M). Then, charged anhydrous K$_2$CO$_3$ granules (6.0 Kg, 43.41 M) into the reactor at 25-30° C. Stirred the reaction mass in the reactor for 10 minutes and charged morpholine (3.3 Kg, 37.88 M). The contents of the reactor were stirred for 15 minutes at 25-30° C. The temperature of the reaction mass was raised slowly to reflux (80-82° C.) and maintained at reflux for 4 hours while monitoring the progress of the reaction every two hours by HPLC.

Analysis of the sample by HPLC after 4 hours reflux: 89.61% product and 8.83% starting material (SM).

Charged morpholine (253 grams) and K$_2$CO$_3$ (400 grams) and further refluxed. Analysis by of the sample at 7.5 hours: 92.8% product and 5.63% SM. So charged morpholine (506 grams), K$_2$CO$_3$ (810 grams) and acetonitrile (30 L) and heated the mass at reflux for another five hours. Analysis of the sample at 12.5 hours: 96.78% product and 2.06% SM. Again charged K$_2$CO$_3$ (820 grams), morpholine (255 gm) and acetonitrile (40 L) and maintained the mass under reflux. Analysis of the sample at 19.5 hours: 97.52% product and 0.9% SM. The reaction mass was cooled to 30-35° C. and filtered solids through nutsche at 30-35° C. The cake on the nutsche was washed with 15 L acetonitrile. Mother liquors (~210 L filtrate) were taken back into the main reactor (GLR) and kept under stirring at 30-35° C., while workup of the solid cake (22.4 Kg), containing the product along with salts, was going on in another reactor.

Wet weight of cake: 22.4 Kg (contained ~23% product).

Charged 30 L water into another reactor followed by the wet cake obtained after nutsche filtration (22.4 Kg). Stirred the mass for 30 minutes and charged EtOAc (47 L). The mass was stirred 15 minutes and settled for 15 minutes. The organic layer containing the product was collected in dedicated containers. pH of the aqueous mother liquors was found to be 10.05 on pH meter.

2$^{nd}$ Extraction:

Charged the above obtained aqueous layer into the reactor followed by EtOAc (47 L). The mass was stirred 15 minutes and settled for 15 minutes and layers separated. The organic layer containing the product was collected in dedicated containers.

3$^{nd}$ Extraction:

Charged the above obtained aqueous layer into the reactor followed by EtOAc (40 L). The mass was stirred 15 minutes and settled for 15 minutes and layers separated. The organic layer containing the product was collected in dedicated containers.

The combined organic layer was dried over sodium sulfate (9.4 Kg) and the clean organic layer was taken for distillation under reduced pressure (>500 mm Hg) at 50-55° C. The mass was cooled to 25-30° C. Added 23.5 L of acetonitrile and stirred well.

Part of the reaction mass (65 L of acetonitrile solution) from GLR was unloaded and charged into the above reaction mass at 25-30° C. and stirred 30 minutes, whereby a clear solution was obtained. The mass was transferred to the main reactor. Washing was given to this reactor with 20 L fresh acetonitrile at 40-45° C. and again transferred to the main reactor and stirred 15 minutes before sampling.

The final, uniformly mixed reaction mass was sampled from the main GLR and analyzed. HPLC: 99.09% product and 0.31% SM. So charged morpholine (510 grams) and K$_2$CO$_3$ (825 grams) and the mass was heated to reflux and further maintained the mass at reflux temperature for 2 hours. A sample was analyzed after 2 hours reflux. Starting material was absent (product purity: 99.24%).

The reflux was further continued for another 2 hours and then cooled the mass temperature to 30-35° C. Solvent was distilled off under reduced pressure (>500 mm Hg), maintaining mass temperature below 55° C.

1$^{st}$ Extraction:

Charged DM water (23.5 L) to the residual mass at 25-30° C. Stirred the mass for 15 minutes and charged ethyl acetate (80 L). A clear solution was obtained. Stirred the mass for 15 minutes and settled the mass for 15 minutes. Layers separated and the product organic layer collected in dedicated containers.

2$^{nd}$ Extraction:

The aqueous layer obtained as above (pH was found to be 9.9 on meter) was charged into the reactor followed by ethyl acetate (40 L). Stirred the mass for 15 minutes and settled the mass for 15 minutes. Layers separated and the product organic layer collected in dedicated containers.

3$^{nd}$ Extraction:

The aqueous layer obtained as above was once again charged into the reactor followed by ethyl acetate (40 L). Stirred the mass for 15 minutes and settled the mass for 15 minutes. Layers separated and the product organic layer collected in dedicated containers.

Brine Washing:

The combined organic layer was taken in the reactor and charged ~35 L brine solution (prepared by dissolving 9.4 Kg sodium chloride in 28.2 L DM water). The mass was stirred for 15 minutes and settled for 30 minutes. Layers separated and collected aqueous layer in dedicated containers.

The organic product layer was dried over anhydrous sodium sulfate (18.8 Kg). Total volume of the organic layer was 185 L. The solvent was distilled off under reduced pressure (>500 mm Hg) maintaining mass temperature below 55° C. Solid mass (Step-5 material) separated in reactor.

Yield: Quantitative;
Purity: 99.51%;
$^1$H-NMR (CDCl$_3$, δ ppm): 1.65-2.04 (12H, m), 2.61-2.63 (6H, m), 2.69-2.77 (1H, m), 3.12 (2H, s), 3.76-3.78 (4H, m), 4.26-4.27 (1H, m), 6.87-6.89 (2H, d, J=8.82 Hz), 7.43-7.45 (2H, d, J=8.80 Hz), 8.91 (1H, s);
Mass (m/z): 374.4 (M+H)$^+$.

Step (vi): Preparation of N-[4-(1-Cyclobutyl piperidin-4-yloxy) phenyl]-2-(morpholin-4-yl) acetamide dihydrochloride Charged isopropyl alcohol (75 L) into the reactor containing step (v) product. The reaction mass temperature was raised to 50-55° C. and stirred for 30 minutes to obtain a clear solution. The mass was cooled to 25° C. before starting the addition of isopropanolic hydrochloride (Isopropanolic HCl).

Isopropanolic HCl (16.2 L, 16.1% w/v) was diluted with isopropanol (8 L) and charged into a holding tank. Isopropanolic HCl in the holding tank was transferred slowly into the reactor in 90 minutes, maintaining mass temperature ~22-28° C. (now and then giving jerks with brine in the reactor jacket). The resulting mass was further stirred under maintenance at 25-30° C. for 6 hours. The mass was centrifuged; the cake on the centrifuge was washed with fresh isopropanol, 16 L (for slurry wash)+5.5 L (for spray wash) and spin dried to obtain 20.26 Kg of wet product. Purity: 99.37%. The material was unloaded into trays and dried in a VTD at 50-60° C. for 16 hours.

Final weight: 12.62 Kg;
Yield: 97%;
$^1$H-NMR (δ ppm, DMSO): 1.65-2.0 (4H, m), 2.13-2.19 (4H, m), 2.33-2.48 (2H, m), 2.8-3.42 (6H, m), 3.67-3.92 (6H, m), 4.16 (2H, s), 4.49-4.70 (2H, m), 6.97-7.03 (2H, m), 7.51-7.54 (2H, m), 10.54 (1H, bs), 10.73 (1H, bs), 11.01 (1H, bs);
Mass (m/z): 374.4 (M+H)$^+$.

Step (vii): Recrystallization of N-[4-(1-Cyclobutyl piperidin-4-yloxy) phenyl]-2-(morpholin-4-yl) acetamide dihydrochloride The reaction was done in a GLR reactor under nitrogen blanket. Methanol (24.8 L) was charged into a GLR followed by addition of above obtained technical material (6.2 Kg, 13.89 M) at 25-30° C. The mass was stirred for 30 minutes to obtain a clear solution. Filtered the mass through nutsche and washed the nutsche with methanol (6.2 L). The filtrate and washing were charged into a clean GLR at 25-30° C.

The contents of the reactor were heated to 62-63° C., where a gentle reflux of methanol started. Addition of isopropanol (31 L) through the addition tank started at this temperature of ~62° C. Addition of isopropanol was completed in one hour, while maintaining mass temperature at 62-63° C. The mass was allowed to cool on its own to room temperature by applying air in the jacket. Solids were separated in the reactor at 48° C. in 3 hours. The mass was allowed to cool to ~35° C. on its own. The mass was further cooled to ~15-20° C. in 2 hours (brine jerks given to the reactor jacket) and the temperature was maintained at ~15-20° C. for 15 minutes.

The mass was centrifuged. The wet cake on the filter was washed with isopropanol (slurry wash) using 9 L isopropanol at 25-30° C. The mass was spin dried in the centrifuge for 1 hour, unloaded (wet weight: 5.0 Kg) taken to vacuum tray drier and dried at 50-60° C. for 12 hours.

Weight of the product: 4.20 Kg;
Yield: 67.7%;
HPLC purity (gradient): 99.71%;
Any other impurity: <0.1%;
Salt content (di HCl): 16.16%;
Melting Range: 247.0-249.5° C.;
DSC (2° C./min, onset): 246.41° C.
TGA (5° C./min): 0.45%
Chemical Assay (% w/w): 101.53%;
IR (cm$^{-1}$): 3280, 3085, 2935, 2498, 1689, 1604, 1552, 1505, 1235, 1120 and 830.
$^1$H-NMR (δ ppm, DMSO): 1.62-2.0 (4H, m), 2.12-2.16 (4H, m), 2.37-2.42 (2H, m), 2.78-2.91 (2H, m), 3.16-3.60 (6H, m), 3.66-3.91 (5H, m), 4.17 (2H, s), 4.47-4.70 (1H, m), 6.96-7.03 (2H, m), 7.52-7.56 (2H, m), 10.69 (1H, bs), 10.86-10.89 (1H, bd), 11.36-11.37 (1H, bd);

Mass (m/z): 374.4 (M+H)$^+$.

$^{13}$C-NMR (DMSO, δ ppm): 13.48, 13.61, 24.94, 25.10, 25.98, 27.89, 43.85, 47.06, 52.00, 57.08, 58.16, 63.38, 67.29, 71.20, 116.33, 117.07, 121.36, 132.02, 132.24, 153.03, 153.37, 162.43.

Advantages of the Invention

1. The current process is a simple seven step process and utilizes commercially available starting materials, which makes the process economical and industrially viable.
2. The current process is devoid of silica gel column purifications, which otherwise make it unsuitable for large scale synthesis.
3. At Step (ii), the current process replaces high boiling solvent dimethyl formamide with low boiling and highly water soluble solvent THF.
4. The current process avoids the usage of highly pyrophoric and flammable reagents like Pd/C and hydrogen gas and instead uses highly economical and environment friendly reagents like iron and ammonium chloride for reduction at Step (iii).
5. At Step (iv), the current process advantageously replaces the halo hydrocarbon solvent, dichloromethane with tetrahydrofuran. Also in this step, the reagent potassium carbonate substitutes triethylamine as an acid scavenger, thus avoiding costly and volatile organic reagent.
6. At Step (vi), the process replaces highly flammable solvent, diethyl ether with isopropanol, thus making the procedure commercially viable.
7. The final product, N-[4-(1-Cyclobutyl piperidin-4-yloxy) phenyl]-2-(morpholin-4-yl) acetamide dihydrochloride obtained in the current process is >99.7% HPLC purity.
8. Overall the current process avoided the use of pyrophoric, flammable and hazardous reagents and solvents and the process also avoided laborious chromatographic purification procedures, thus making it a safe, simple and economically viable process for the large scale production.

We claim:
1. A process for production of N-[4-(1-cyclobutyl piperidin-4-yloxy) phenyl]-2-(morpholin-4-yl) acetamide dihydrochloride of formula (I), comprising:

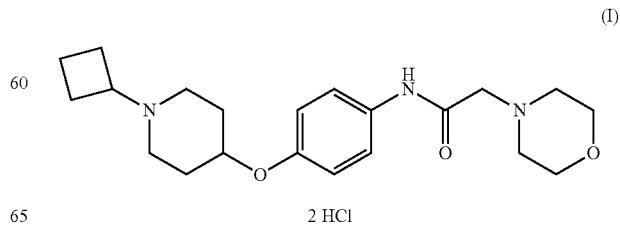

(I)

2 HCl

Step (i): reacting 4-hydroxy piperidine of formula (1) with cyclobutanone of formula (2)

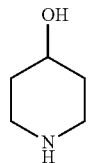
(1)

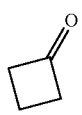
(2)

in presence of sodium triacetoxy borohydride in ethylene dichloride at a temperature in the range of 20° C. to 30° C. for a period of 12 hours to 14 hours to obtain 1-cyclobutylpiperidin-4-ol of formula (3);

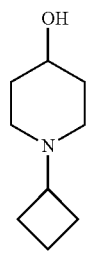
(3)

Step (ii): reacting 1-cyclobutylpiperidin-4-ol of formula (3) with 4-fluoro-1-nitrobenzene of formula (4)

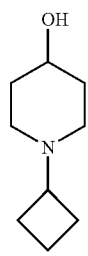
(3)

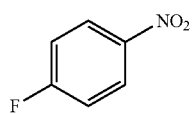
(4)

in tetrahydrofuran and sodium hydride at a temperature in the range of 30° C. to 45° C. for a period of 5 hours to 6 hours to obtain 4-(1-cyclobutylpiperidin-4-yloxy)-1-nitrobenzene of formula (5) and purifying the compound of formula (5) using 10% aqueous acetic acid solution at 25° C. to 30° C.;

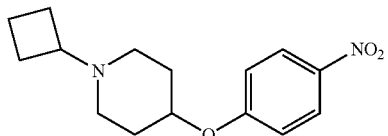
(5)

Step (iii): reducing 4-(1-cyclobutylpiperidin-4-yloxy)-1-nitrobenzene of formula (5) by using ammonium chloride and iron powder in water and ethyl alcohol at a temperature in the range of 70° C. to 85° C. for a period of 3 hours to 5 hours to obtain 4-(1-cyclobutylpiperidin-4-yloxy) aniline of formula (6);

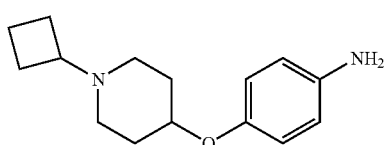
(6)

Step (iv): reacting 4-(1-cyclobutylpiperidin-4-yloxy) aniline of formula (6) with chloroacetylchloride of formula (7)

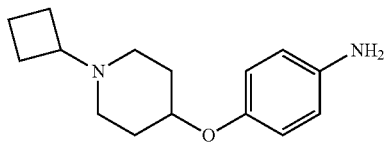
(6)

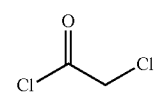
(7)

in tetrahydrofuran and potassium carbonate at a temperature in the range of −10° C. to 0° C. for a period of 4.5 hours to 5.5 hours to obtain 2-chloro-N-[4-(1-cyclobutyl piperidin-4-yloxy) phenyl] acetamide of formula (8) and recrystallizing the compound of formula (8) using isopropanol and methanol under reflux for a period of 0.5 to 1 hour;

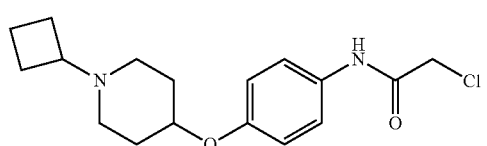
(8)

Step (v): reacting 2-chloro-N-[4-(1-cyclobutyl piperidin-4-yloxy)phenyl]acetamide of formula (8) with morpholine of formula (9)

(8)

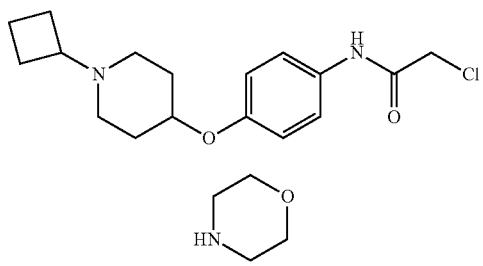

(9)

in acetonitrile and potassium carbonate at a temperature in the range of 75° C. to 85° C. for a period of 20 hours to 30 hours to obtain N-[4-(1-cyclobutyl piperidin-4-yloxy) phenyl]-2-(morpholin-4-yl) acetamide of formula (10);

(10)

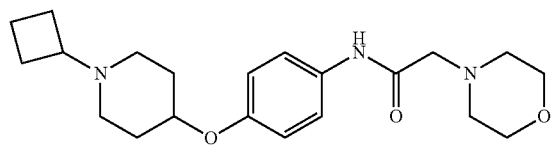

Step (vi): reacting N-[4-(1-Cyclobutyl piperidin-4-yloxy) phenyl]-2-(morpholin-4-yl) acetamide of formula (10) in presence of isopropanolic hydrochloride and isopropanol (10)

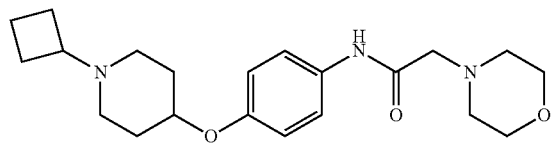

at a temperature in the range of 20° C. to 30° C. for a period of 7 hours to 8.5 hours to obtain N-[4-(1-Cyclobutyl piperidin-4-yloxy) phenyl]-2-(morpholin-4-yl) acetamide dihydrochloride of formula (11);

(11)

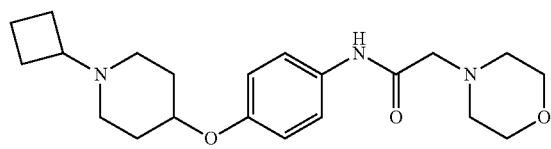

2 HCl

Step (vii): recrystallization of N-[4-(1-Cyclobutyl piperidin-4-yloxy) phenyl]-2-(morpholin-4-yl) acetamide dihydrochloride of formula (11)

(11)

2 HCl in presence of isopropanol and methanol at a temperature in the range of 58° C. to 63° C. for a period of 4 hours to 5 hours to obtain N-[4-(1-cyclobutyl piperidin-4-yloxy) phenyl]-2-(morpholin-4-yl) acetamide dihydrochloride of formula (I).

2. The process as claimed in claim 1, wherein the temperature used in Step (i) is 25° C. to 30° C.

3. The process as claimed in claim 1, wherein the duration of reaction in Step (i) is 13 hours to 13.5 hours.

4. The process as claimed in claim 1, wherein the temperature used in Step (ii) is 35° C. to 40° C.

5. The process as claimed in claim 1, wherein the duration of reaction in Step (ii) is 5.5 to 6 hours.

6. The process as claimed in claim 1, wherein the temperature used in Step (iii) is 75° C. to 80° C.

7. The process as claimed in claim 1, wherein the duration of reaction in step (iii) is 4 hours.

8. The process as claimed in claim 1, wherein the temperature used in Step (iv) is −10° C. to −5° C.

9. The process as claimed in claim 1, wherein the duration of reaction in Step (iv) is 5 hours.

10. The process as claimed in claim 1, wherein the temperature used in Step (v) is 80° C. to 82° C.

11. The process as claimed in claim 1, wherein the duration of reaction in Step (v) 24 hours to 26 hours.

12. The process as claimed in claim 1, wherein the temperature used in Step (vi) is 25° C. to 30° C.

13. The process as claimed in claim 1, wherein the duration of reaction in Step (vi) is 7.5 hours to 8 hours.

14. The process as claimed in claim 1, wherein the temperature used in Step (vii) is 62° C. to 63° C.

15. The process as claimed in claim 1, wherein the duration of reaction in Step (vii) is 4.5 hours.

16. The process as claimed in claim 1, wherein the purity of N-[4-(1-cyclobutyl piperidin-4-yloxy) pheynyl]-2-(morpholin-4-yl) acetamide dihydrochloride of formula (I) is >99.7%.

* * * * *